(12) United States Patent
Werner (10) Patent No.: US 9,636,134 B2
(45) Date of Patent: May 2, 2017

(54) SURGICAL CUTTING DEVICE AND METHODS OF USING SAME

(71) Applicant: UNIVERSITY OF ALASKA ANCHORAGE, Anchorage, AK (US)

(72) Inventor: Samuel Werner, Tucson, AZ (US)

(73) Assignee: University of Alaska Anchorage, Anchorage, AK (US)

(*) Notice: Subject to any disclaimer, the term of this patent is extended or adjusted under 35 U.S.C. 154(b) by 225 days.

(21) Appl. No.: 14/516,260

(22) Filed: Oct. 16, 2014

(65) Prior Publication Data

US 2015/0112373 A1   Apr. 23, 2015

Related U.S. Application Data

(60) Provisional application No. 61/892,199, filed on Oct. 17, 2013.

(51) Int. Cl.
*A61B 17/32* (2006.01)
*A61B 17/00* (2006.01)
*A61B 17/3211* (2006.01)

(52) U.S. Cl.
CPC ... *A61B 17/320068* (2013.01); *A61B 17/3211* (2013.01); *A61B 2017/00734* (2013.01); *A61B 2017/320072* (2013.01); *A61B 2017/320096* (2013.01)

(58) Field of Classification Search
CPC .......... A61B 17/148; A61B 17/320068; A61B 17/22004; A61B 17/22012; A61B 2017/320072; A61B 2017/320096; A61F 9/00745
See application file for complete search history.

(56) References Cited

U.S. PATENT DOCUMENTS

| | | | | |
|---|---|---|---|---|
| 4,989,588 A | * | 2/1991 | Kubota | ............ A61B 17/22012 601/4 |
| 6,267,594 B1 | * | 7/2001 | Hugo | ..................... A61B 17/14 433/119 |
| 7,758,600 B2 | | 7/2010 | Beaupre | |
| 2007/0249942 A1 | * | 10/2007 | Salehi | ................. A61F 9/00745 600/471 |
| 2009/0163940 A1 | * | 6/2009 | Sliwa | ............... A61B 17/22012 606/159 |

OTHER PUBLICATIONS

Product Data Sheet—Pico Vibe 10mm Vibration Motor—2.7mm Type, Model: 310-103, Precision Microdrives (2013) (6 pages).

* cited by examiner

*Primary Examiner* — Sarah W Aleman
(74) *Attorney, Agent, or Firm* — Ballard Spahr LLP (57) ABSTRACT

A vibrational assembly for operative coupling to a surgical cutting element. The vibrational assembly receives a portion of the surgical cutting element and imparts vibration to the surgical cutting element within a single plane. In combination, the vibrational assembly and the surgical cutting element form a surgical cutting device.

24 Claims, 7 Drawing Sheets

SURGICAL CUTTING DEVICE AND METHODS OF USING SAME

This application claims priority to U.S. Provisional Patent Application No. 61/892,199, entitled "Surgical Cutting Device and Methods of Using Same," which was filed Oct. 17, 2013, and which is hereby incorporated herein by reference in its entirety.

FIELD

This invention relates to surgical cutting devices and, more particularly, to surgical cutting devices that vibrate a cutting element within a single selected plane.

BACKGROUND

Existing surgical cutting instruments frequently encounter significant drag as they are advanced through tissue. Use of these surgical cutting instruments often results in significant tissue damage, imprecise incisions, long healing times, and poor closure of incisions. Even motorized cutting instruments fail to sufficiently address these problems. For example, ultrasonic surgical cutting instruments vibrate in multiple planes at high frequencies, making it difficult to form clean incisions and/or avoid unnecessary tissue damage. Moreover, ultrasonic surgical cutting instruments generate undesirable levels of heat.

Thus, there is a need in the pertinent art for surgical cutting instruments that easily pass through tissue to form precise incisions while avoiding significant tissue damage, long healing times, and poor incision closure.

SUMMARY

Described herein is a vibrational assembly for operative coupling to a surgical cutting element. The vibrational assembly can have a longitudinal axis and comprise an elongate housing having an inner surface and an outer surface. The inner surface of the elongate housing can define a receiving space. The receiving space can be configured to securely receive a portion of the surgical cutting element. The vibrational assembly also comprises a vibrational motor secured within the receiving space of the elongate housing. The vibrational assembly further comprises a power source operatively coupled to the vibrational motor. The vibrational motor can be configured for operative coupling to the cutting element within the receiving space of the elongate housing such that, upon activation of the vibrational motor, the vibrational motor is configured to effect vibration of the cutting element in a single desired plane. Upon receipt of the surgical cutting element within the vibrational assembly, the vibrational assembly and the surgical cutting element can cooperate to form a surgical cutting device.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a power source" can include two or more such power sources unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Figure 1:
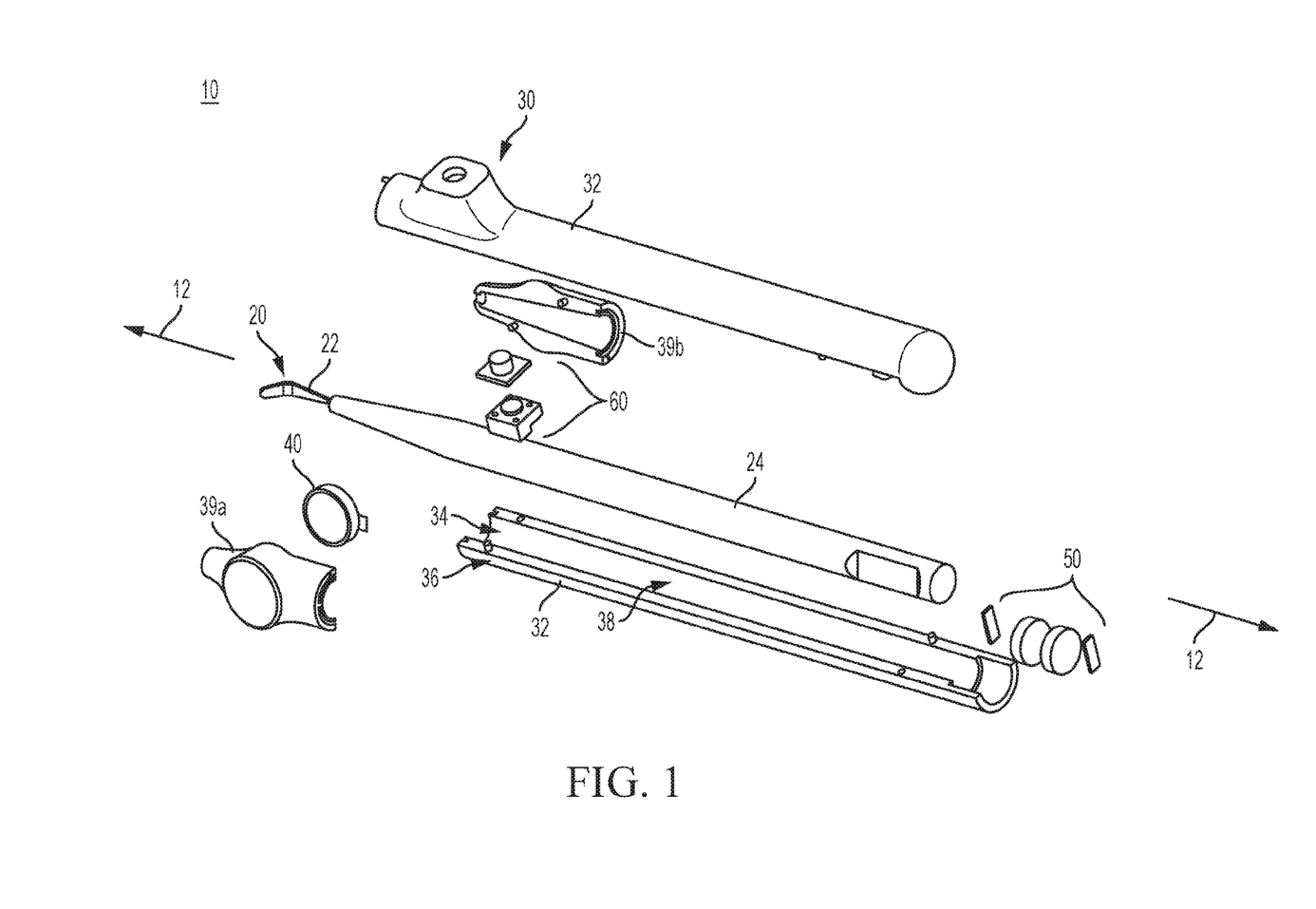
FIG. 1 is an exploded view of an exemplary surgical cutting device as disclosed herein.
Figure 2:
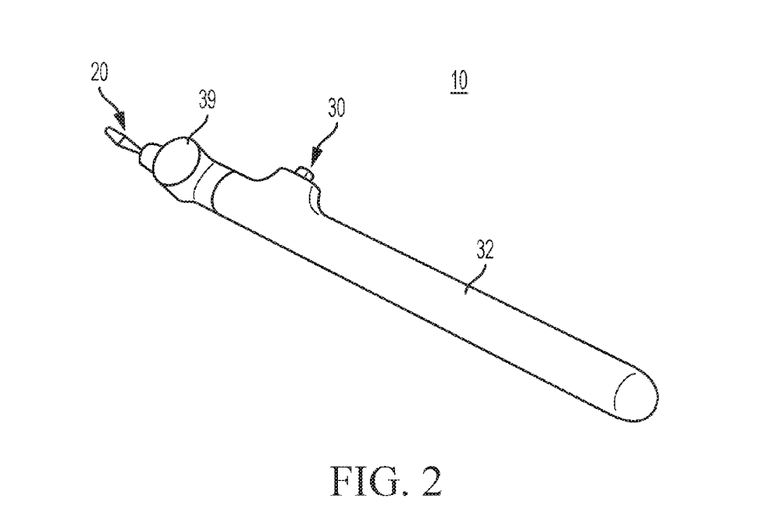
FIG. 2 is an image showing a perspective view of an exemplary assembled surgical cutting device as disclosed herein.
Figure 3:
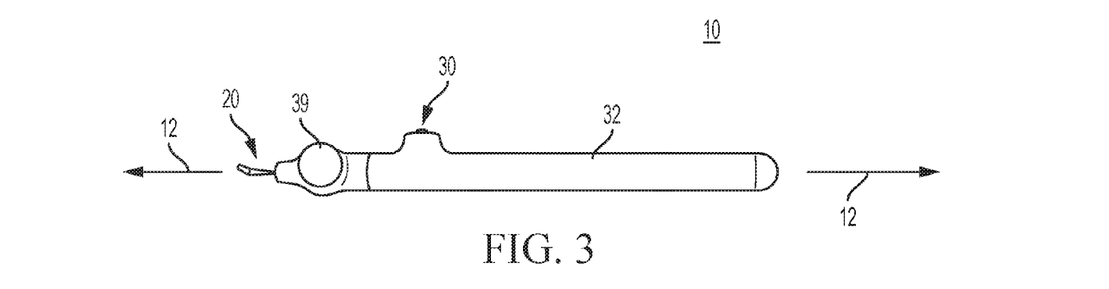
FIG. 3 is an image showing a side elevational view of the surgical cutting device of FIG. 2.

Described herein with reference to FIGS. 1-3 are (i) a vibrational assembly 30 configured for operative coupling to a surgical cutting element 20 and (ii) a surgical cutting device 10 comprising the vibrational assembly 30 and the surgical cutting element 20. In exemplary aspects, the vibrational assembly 30 and surgical cutting device 10 can have a common longitudinal axis 12. It is contemplated that the vibrational assembly 30 disclosed herein can be employed to improve the performance of a conventional surgical element during the making of an incision and/or the penetration of lamellar tissue within a subject. It is contemplated that the vibrational assembly 30 and surgical cutting device 10 disclosed herein can be configured to reduce drag when the surgical cutting element 20 is passed through a selected tissue region of a subject, thereby reducing tugging or tearing action between the blade and tissue. It is further contemplated that the vibrational assembly 30 and surgical cutting device 10 disclosed herein can be configured to permit more precise dissection of layered tissue than is achievable with conventional surgical cutting elements. It is still further contemplated that the reduction in drag and improved precision achieved by the disclosed surgical cutting device 10 can minimize tissue damage and reduce healing time. It is still further contemplated that the disclosed surgical cutting device 10 can produce incisions having smoother bonding surfaces than those produced by conventional cutting devices, thereby leading to improved closure of surgical incisions by self-sealing.

In one aspect, the vibrational assembly 30 can comprise an elongate housing 32 having an inner surface 34 and an outer surface 36. In this aspect, the inner surface 34 of the elongate housing 32 can define a receiving space 38. It is contemplated that the receiving space 38 can be configured to securely receive a portion of the surgical cutting element 20. It is further contemplated that the receiving space 38 can generally conform to the shape of the portion of the surgical cutting element 20 positioned within the receiving space. As shown in FIGS. 1-3, it is contemplated that the elongate housing 32 can optionally be substantially cylindrical. In exemplary aspects, the cutting element 20 can have a cutting portion 22 and a shaft portion 24.

In another aspect, the vibrational assembly 30 can comprise a vibrational motor 40 secured within the receiving space 38 of the elongate housing 32. It is contemplated that the vibrational motor 40 can be any conventional miniature vibrational motor. In exemplary aspects, the vibrational motor 40 can be selectively adjustable to vary one or more operational parameters, including, for example and without limitation, vibrational frequency. In one exemplary aspect, it is contemplated that the vibrational motor 40 can be a Pico Vibe™ vibrational motor (PRECISION MICRODRIVES LIMITED). In another exemplary aspect, it is contemplated that the vibrational motor 40 can be an eccentric rotating mass (ERM) motor.

In an additional aspect, the vibrational assembly 30 can comprise a power source 50 operatively coupled to the vibrational motor 40. Optionally, in this aspect, the power source 50 can be positioned within the receiving space 38 of the elongate housing 32. In exemplary aspects, the power source 50 can be a battery. In these aspects, it is contemplated that the power source 50 can be positioned proximate a proximal portion of the housing 32 (opposite a distal portion of the housing proximate the cutting portion 22 of the cutting element 20). In other optional aspects, the power source 50 can be an external power source as is known in the art. In these aspects, it is contemplated that the vibrational assembly 30 can further comprise an electrical cable configured to provide operative electrical communication between the vibrational motor 40 and the external power source 50.

Figure 4A:
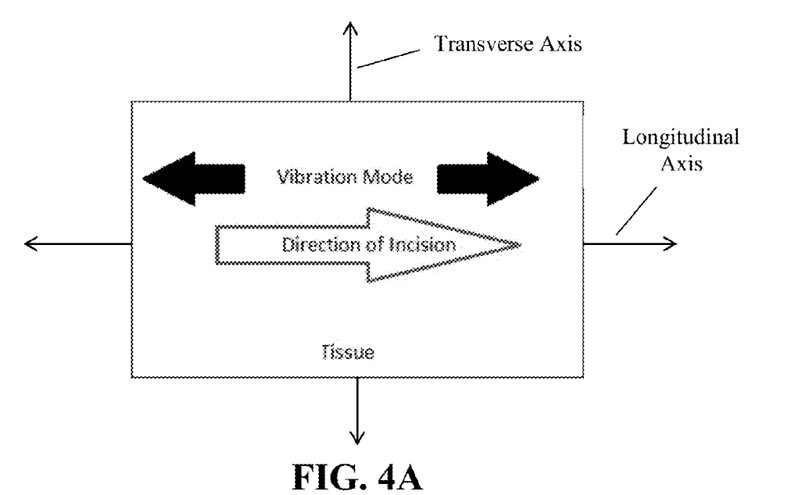
FIG. 4A is a schematic diagram depicting the application of vibration in a direction that is substantially parallel to or in alignment with a direction of incision within a tissue, as viewed from the top of the tissue.
Figure 4B:
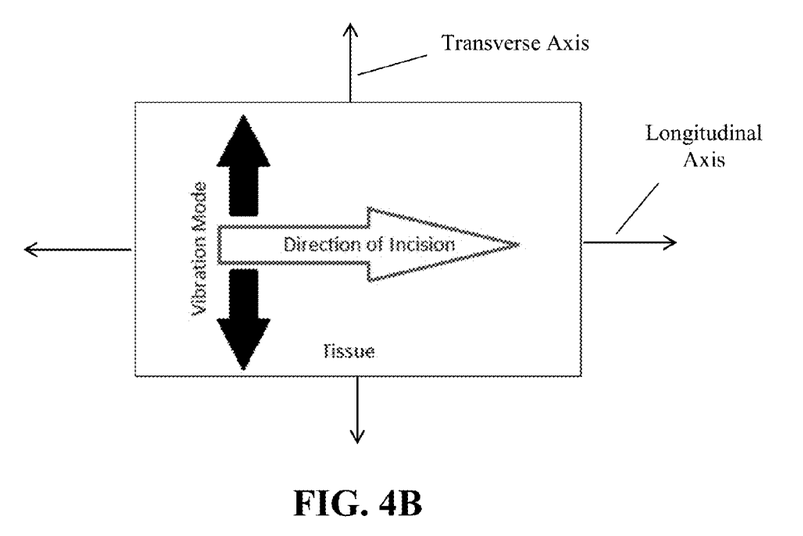
FIG. 4B is a schematic diagram depicting the application of vibration in a direction that is substantially perpendicular or transverse to a direction of incision within a tissue, as viewed from the top of the tissue.
Figure 4C:
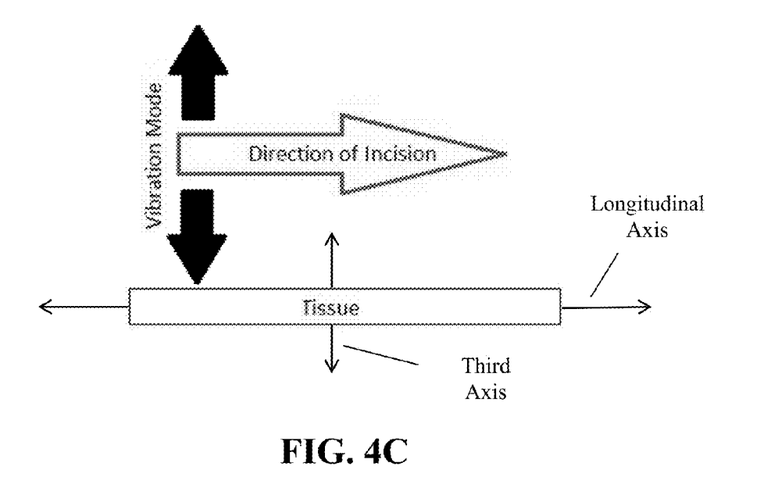
FIG. 4C is a schematic diagram depicting the application of vibration in a direction that is substantially perpendicular to a direction of incision within a tissue, as viewed from the side of the tissue. The vibration depicted in FIGS. 4A and 4B occurs substantially within a plane defined by a longitudinal axis and a transverse axis of the tissue. In contrast, the vibration depicted in FIG. 4C occurs in a direction that is substantially parallel or in alignment with a third axis of the tissue, which is substantially perpendicular to the plane defined by the longitudinal axis and the transverse axis of the tissue.

In a further aspect, the vibrational motor 40 can be configured for operative coupling to the cutting element 20 within the receiving space 38 of the elongate housing 32 such that, upon activation of the vibrational motor, the vibrational motor is configured to effect vibration of the cutting element in a single desired plane. Exemplary vibrational profiles created by the disclosed cutting device 10 (and vibrational assembly 30) are shown in FIGS. 4A-4C. FIG. 4A depicts the application of vibration in a direction that is substantially parallel to or in alignment with a direction of incision within a tissue, as viewed from the top of the tissue. FIG. 4B is a schematic diagram depicting the application of vibration in a direction that is substantially perpendicular or transverse to a direction of incision within a tissue, as viewed from the top of the tissue. FIG. 4C is a schematic diagram depicting the application of vibration in a direction that is substantially perpendicular to a direction of incision within a tissue, as viewed from the side of the tissue. In exemplary aspects, as shown in FIGS. 4A-4B, the vibration can occur substantially within a single desired plane that is defined by a longitudinal axis and a transverse axis of the tissue. Alternatively, in other exemplary aspects and as shown in FIG. 4C, the vibration can occur within a single desired plane that is substantially perpendicular to the plane defined by the longitudinal axis and the transverse axis of the tissue. In these aspects, the single desired plane of vibration can be parallel or in alignment with a third (optionally, vertical) axis of the tissue, which can be substantially perpendicular to both the longitudinal axis and the transverse axis of the tissue.

In exemplary aspects, the receiving space 38 can comprise a receptacle 39 that substantially conforms to the shape of the vibrational motor 40. In additional exemplary aspects, the receptacle 39 can be integrally formed with the remaining portions of the elongate housing 32. Alternatively, in other exemplary aspects, the receptacle 39 can be a discrete component that is securely (and, optionally, removably) attached to the distal portion of the housing 32. In these aspects, it is contemplated that the receptacle 39 can comprise at least two receptacle elements 39a, 39b that are configured for engagement with one another, thereby forming the receptacle 39. It is contemplated that the engagement between the two receptacle elements 39a, 39b can be detachable mechanical engagement using any conventional means.

In exemplary aspects, it is contemplated that the vibrational motor 40 can have a longitudinal axis, and the vibrational motor 40 can be mounted substantially parallel to the longitudinal axis 12 of the cutting element 20 to thereby generate oscillation in an incision plane (the plane in which the incision is made). In additional exemplary aspects, the longitudinal axis of the vibrational motor 40 can optionally be positioned proximate the distal portion of the housing 32 proximate the cutting portion 22 of the cutting element 20. However, it is contemplated that any selected placement of the vibrational motor 40 can be used. In exemplary aspects, the vibrational motor 40 can be mounted on a top portion of the surgical cutting device 10 to produce additional clearance on the underside of the device. It is contemplated that this configuration can be advantageous for use with small surgical windows. In other exemplary aspects, the vibrational motor 40 can be mounted on an underside of the surgical cutting device 10 to reduce visual obstruction.

In yet another aspect, the vibrational assembly 30 can further comprise an on-off switch 60 operatively coupled to the vibrational motor 40. In this aspect, it is contemplated that the on-off switch 60 can be configured to permit selective activation of the vibrational motor 40. It is further contemplated that the on-off switch 60 can be accessible from outside the receiving space 38 of the elongate housing 32. In exemplary aspects, at least a portion of the on-off switch 60 can be accessible through an opening defined between the inner and outer surfaces 34, 36 of the housing 32. In these aspects, it is contemplated that portions of the inner and outer surfaces 34, 36 of the housing 32 proximate the opening can be shaped to conform to the shape of the on-off-switch. In other exemplary aspects, the on-off switch 60 can be selected from the group consisting of a toggle switch, a rotary switch, and a push-button switch. However, it is contemplated that any conventional on-off switch can be used.

In some exemplary aspects, it is contemplated that the orientation of the vibrational motor 40 within the receiving space 38 of the elongate housing 32 can be selectively adjustable to vary the plane in which the cutting portion 22 of the cutting element 20 vibrates. In these aspects, it is contemplated that the vibrational motor can be selectively accessible, and that the cutting device 10 can be configured to support the vibrational motor in a variety of orientations. For example, the receptacle elements 39a, 39b can be selectively detachable to permit access to the vibrational motor, and the receptacle 39 can be configured to securely receive the vibrational motor in a plurality of operative positions, wherein each operative position corresponds to a different orientation of the vibrational motor that is configured to produce a corresponding vibrational profile. In additional exemplary aspects, it is contemplated that the vibrational motor 40 can operate at a vibrational frequency that is selectively adjustable. In these aspects, it is contemplated that the vibrational frequency can range from about 0 kHz to about 20 kHz. In some exemplary aspects, the vibrational frequency can range from about 0 kHz to about 5 kHz. In additional exemplary aspects, the vibrational frequency can range from about 100 Hz to about 500 Hz. In still other exemplary aspects, the vibrational frequency can be about 200 Hz.

In further exemplary aspects, it is contemplated that the receiving space 38 of the elongate housing 32 can be configured to receive vibrational motors 40 of varying sizes. In other exemplary aspects, the elongate housing 32 can be configured to permit selective axial movement of the surgical cutting element 20 relative to the longitudinal axis 12, thereby permitting adjustment of the axial distance between the cutting element and the vibrational motor 40. In still other exemplary aspects, the elongate housing 32 can be configured to permit selective rotation of the surgical cutting element 20 relative to the longitudinal axis 12, thereby permitting adjustment of the relative angular orientation between the cutting element 20 and the vibrational motor 40.

As shown in FIGS. 1-3, it is contemplated that, upon receipt of a cutting element 20 within the vibrational assembly 30, the vibrational assembly and the cutting element can cooperate to form a surgical cutting device 10. In exemplary aspects, at least a portion of the shaft portion 24 of the cutting element 20 can be securely received within the receiving space 38 of the elongate housing 32. It is contemplated that the vibrational motor 40 can be operatively coupled to the cutting element 20 within the receiving space 38 of the elongate housing 32 such that, upon activation of the vibrational motor, the cutting portion 22 of the cutting element is configured to vibrate in the single desired plane.

It is contemplated that the cutting element 20 can be any conventional surgical cutting element known in the art. In exemplary aspects, the cutting element 20 can be a conventional surgical blade, such as, for example and without limitation, a surgical blade manufactured by BEAVER BLADES or a surgical blade manufactured by CRESCENT SURGICAL BLADES. In other exemplary aspects, it is contemplated that the cutting element 20 can be a surgical needle holder that is configured to support at least one surgical needle in an operative position. It is contemplated that use of such a surgical needle holder with the disclosed cutting device 10 can be advantageous during endoscopic suturing or cutting, when remote tactile feedback from surgical instruments is typically not possible.

Optionally, in some exemplary aspects and as further described herein, it is contemplated that the cutting element 20 can be selectively axially moveable relative to the longitudinal axis 12, thereby permitting adjustment of the axial distance between the cutting portion 22 of the cutting element and the vibrational motor 40. In further exemplary aspects, it is contemplated that the cutting element 20 can be selectively rotatable relative to the longitudinal axis 12, thereby permitting adjustment of the relative angular orientation between the cutting portion 22 of the cutting element and the vibrational motor 40.

In one exemplary aspect, a method for creating an incision in a selected tissue can comprise operatively positioning the disclosed cutting device relative to the selected tissue. Optionally, in this aspect, the selected tissue can be eye tissue. In another aspect, the method for creating the incision can comprise selectively activating the vibrational motor. In this aspect, and as further disclosed herein, the vibrational motor can be configured to generate vibrations in a single plane. In a further aspect, during activation of the vibrational motor, the method for creating the incision can comprise placing the cutting element of the cutting device into contact with the selected tissue. In still a further aspect, the method for creating the incision can comprise selectively advancing the cutting element to form the incision. Following creation of the incision, the cutting element can be removed from contact with the selected tissue, and the vibrational motor can be inactivated. Optionally, in exemplary aspects, the method for creating the incision can comprise selectively adjusting an orientation of a vibrational motor to thereby adjust a profile of the vibration applied by the vibrational motor. In these aspects, the method can optionally comprise detaching the receptacle elements of the cutting device, adjusting the orientation of the vibrational motor within the receptacle, and reattaching the receptacle elements.

In some exemplary applications, the disclosed surgical cutting device 10 and/or vibrational assembly 30 can be used during surgical operations on the front of an eye of a subject. In particular applications, it is contemplated that the surgical cutting device and vibrational assembly can be used to perform cataract surgeries in developing countries. Although micro-incision of the cornea and phacoemulsification (phaco) of the cataract via ultrasound is the preferred method in the developed world, it is often too technologically demanding and expensive for use in developing countries. Manual small incision cataract surgery (MSICS) is popular in developing nations because it is effective, economical, and relatively easy to learn. As with the phaco technique that is commonly used in developed countries, it relies on a self-sealing incision, but the cataract is broken up and removed manually. This process requires a larger incision, which can increase the risk of complications. As further disclosed herein, it is contemplated that an improvement in incision quality can decrease recovery time and infection risk. Thus, it is contemplated that the use of the disclosed cutting device and/or vibrational assembly can produce more precise incisions that have better self-sealing characteristics, which, in turn, can greatly improve cataract surgery outcomes in developing regions.

In other exemplary applications, it is contemplated that the disclosed surgical cutting device 10 and/or vibrational assembly 30 can be incorporated into a robotic surgical system as is known in the art, such as, for example and without limitation, the DAVINCI surgical system. In these applications, it is contemplated that the vibrating cutting element 20 of the surgical cutting device 10 can produce reduced tissue drag and improved tissue penetration, thereby minimizing the discordance between the actual handling of the surgical cutting device and what the device operator is feeling.

Experimental Examples

Using ballistics gelatin as a tissue analog, experiments were performed to investigate the performance of a vibrating scalpel relative to a control that does not vibrate. Experiments were performed (a) using a scalpel vibrating perpendicular to the incision as shown in FIG. 4C and (b) using a scalpel without vibration.

In order to quantify incision quality, microscopy was used to determine the surface roughness of the cut produced by scalpels with and without vibration. In addition, the resulting force-velocity response of each vibratory mode was investigated.

Ballistics gelatin conforming to FBI calibration standards was used as a tissue analog. The analog was cut into approximately 2"×1"×4" (H×W×D) pieces and placed into a sample holder. The sample holder was supported by a plain carbon steel pedestal with a gage length of 11.516" and square cross section of side length 0.5". Two Omega strain gages with a nominal resistance of 120Ω, and gage factor of 2.02, were mounted on either side of the pedestal in the direction of the incision. The test frame was fitted with a stepper motor operating at 11V, for each test. A rail system supported the scalpel holder assembly which was mounted to the stepper motor. An eccentric rotating mass (ERM) motor was placed in the scalpel holder so as to cause vibration in a vertical plane as depicted in FIG. 4C. A #5 Beaver blade was used to create the incision and was threaded into the scalpel holder.

The design of the strain gage circuit came about as the result of significant effort and experimentation. Eventually, resulting in the design depicted in FIG. 4 (graphic provided by Jake Plancich). As can be seen, the strain gages are mounted in a Wheatstone bridge so as to compensate for axial forces and temperature effects. In theory, this configuration ensures that all forces experienced by the strain gages will be due to the bending moment created by the scalpel cutting through the ballistics gelatin.

Balancing the bridge, to minimize noise in the unloaded condition, was accomplished through a potentiometer. Noise was further reduced by passing both sides of the Wheatstone bridge through a low pass filter constructed with 10 kΩ resistors and 1 µF capacitors. Two Analog Devices AD623 instrumentation amplifiers were used to create a gain of 10201. The resulting output was sent to an oscilloscope where it was collected for further analysis via Microsoft Excel.

Testing was performed with the strain gage excitation voltage at 2V, and the amplifier voltage set at +5V and −5V. The ERM motor was excited at 3V, and the stepper motor was set to 11V for each test. Prior to each test, the Wheatstone bridge was set to zero by adjusting the potentiometer. A total of ten tests were performed, five with vibration and five without vibration. All five vibratory tests were performed first. After each sample was tested, it was numbered and set aside. A marker was placed at the end of each incision created with vibration. In order to minimize the effects of varying geometry (i.e. depth of cut) each sample was tested once with vibration, and once without. Once testing was completed, the incisions of two samples were marked with water based dye, as suggested by the gelatin's manufacturer, for viewing under light microscopy.

Data analysis was performed using Microsoft Excel. As mentioned previously, as the scalpel moved through the ballistics gel, it exerted a force on the pedestal resulting in a bending moment. In turn, this bending moment caused an excitation in the strain gages, thereby causing an increase in resistance which was measured by the oscilloscope as a change in voltage.

The change in voltage was used to determine strain. After the strain was been determined, the bending moment felt by the strain gages was derived. Once the bending moment was found, the force of the scalpel exerted onto the pedestal was determined.

The oscilloscope captured data in the form of time and voltage, measured in seconds and volts respectively. Raw data for each sample was viewed in charts, where it was determined that a 50 period moving average presented the best interpretation of what was occurring throughout the incision. This moving average is shown in FIG. 5.

Figure 5:
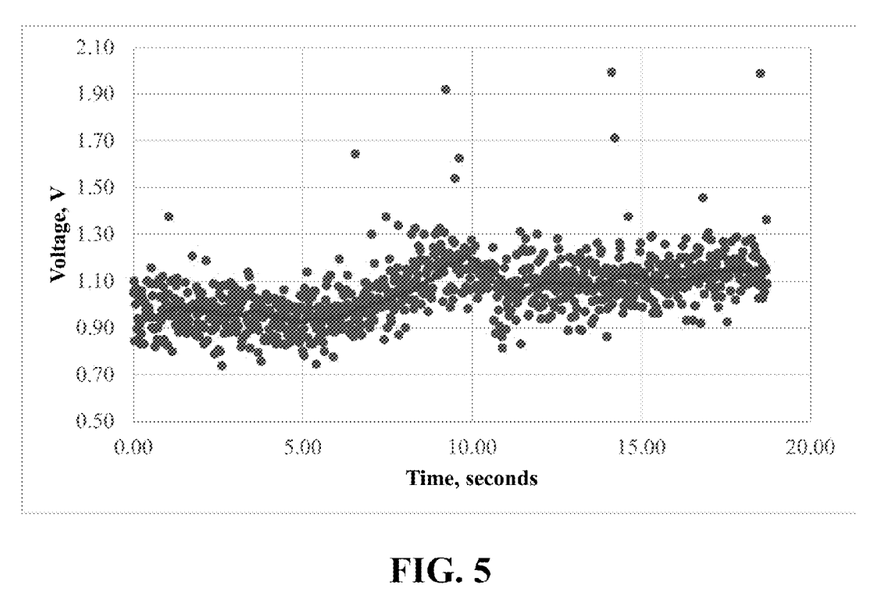
FIG. 5 is a plot of raw voltage versus time for an incision made with vibration as disclosed herein. The center line represents a 50-period moving average of the recorded data.

As can be clearly seen in FIG. 5, even with no load on the strain gages, there was still some voltage output to the oscilloscope. In addition, there was a "toe" region where the scalpel first made impact with the gel (at approximately 5 seconds). The voltage then quickly increased until approximately 10 seconds where the scalpel overcame the resistance of the gelatin and the incision was initiated. The voltage then quickly dropped off and maintained a near steady state for the remainder of the incision. Since there was no load applied from zero to 5 seconds it can be referred to as the "no load" region, and the period after steady state is achieved can be referred to as the "loaded" region. The average value for each of these regions was determined for each test and was used to calculate the average force. In addition, the average no-load value was used to normalize the data for easy comparison between vibration and non-vibration tests.

Figure 6:
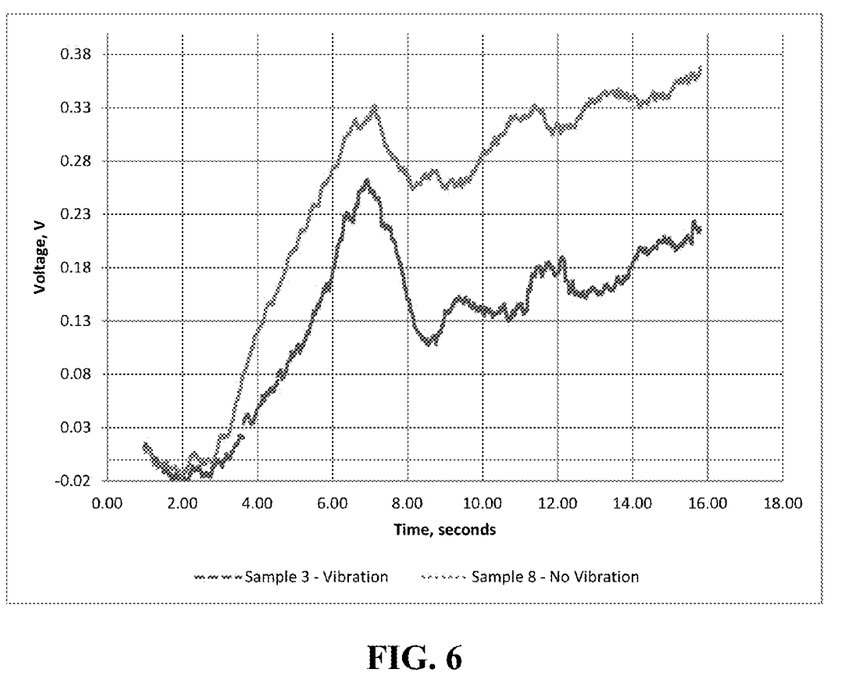
FIG. 6 is a plot of voltage versus time, following normalization, for samples tested with and without vibration. As shown, a no load condition occurs before 2 seconds, and scalpel impact can be seen at approximately 3 seconds. Breakthrough and incision propagation is denoted by the sudden change in voltage between 6 and 8 seconds.

FIG. 6 shows typical voltage over time results for samples tested with vibration and without vibration. These results were normalized to allow for a direct comparison of the relative differences between the two tests. All plots show a 50 period moving average of the raw data.

Figure 7:
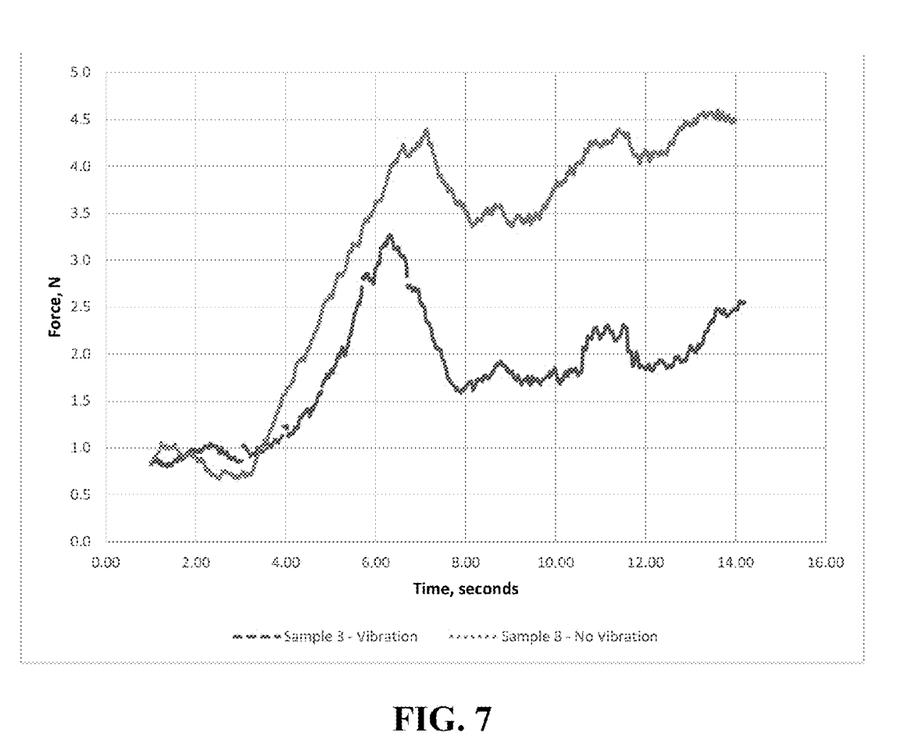
FIG. 7 is a plot of force versus time for the samples characterized in FIG. 6.

Over the course of the tests, the sample with scalpel vibration had a smaller change in voltage. Since force is directly proportional to voltage, it can be said that less force was required to start an incision with a vibrating scalpel. Furthermore, the steady loading region of the vibration test was much lower than the test without vibration, indicating that once the incision has been initiated it is easier to maintain. These results are made clearer in FIG. 7, which is a depiction of force over time for the sample shown in FIG. 6.

The force required to initiate the incision for the sample with vibration was about 2.3 N, whereas the sample without vibration required around 3.5 N. Once the cut was initiated, the force required to propagate the cut increased over time in samples with vibration as well as samples without vibration.

Figure 8:
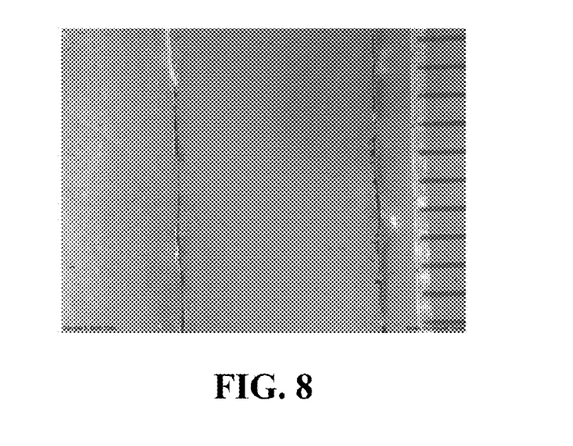
FIG. 8 is an image (at 10× magnification) showing a comparison of incisions created with vibration as disclosed herein (on left) and without vibration (on right). The scale depicted on the right of the image represents 1 mm increments.

Water based food coloring was used to dye both incisions made on one representative sample (Sample 5). They were then viewed under various levels of magnification. A side-by-side comparison is shown in FIG. 8. The incision created with vibration was marked in green dye (shown on the left of FIG. 8). As shown in FIG. 8, at 10× magnification, the cut made without vibration did not appear as smooth as the cut made with vibration.

Figure 9A:
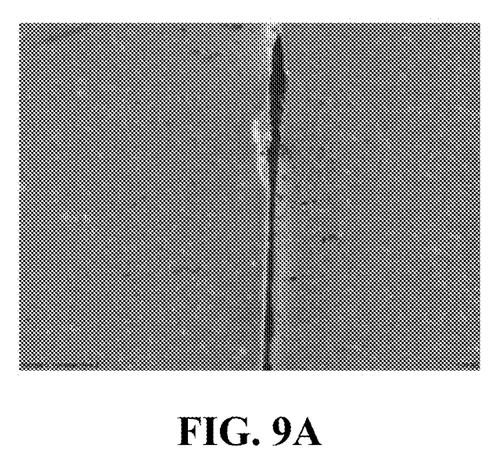
FIG. 9A is an image (at 80× magnification) of an incision created with vibration as disclosed herein.
Figure 9B:
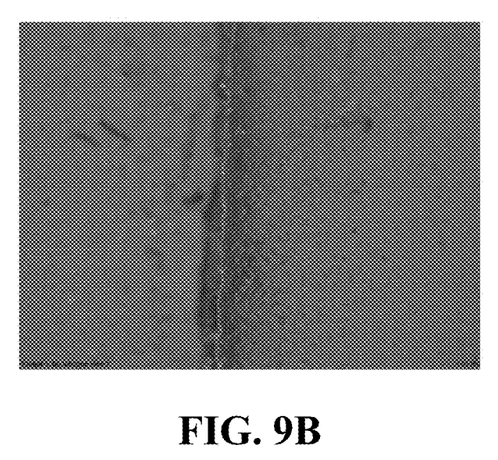
FIG. 9B is an image (at 80× magnification) of an incision created without vibration.

FIGS. 9A and 9B are images of the two incisions (incision with vibration shown in FIG. 9A; incision without vibration shown in FIG. 9B) under 80× magnification. As shown, the incision made without vibration appeared more jagged than the incision made with vibration of the scalpel.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A surgical cutting device, the surgical cutting device having a longitudinal axis and comprising:
    an elongate housing having an inner surface and an outer surface, the inner surface of the elongate housing defining a receiving space;
    a cutting element having a cutting portion and a shaft portion, wherein at least a portion of the shaft portion of the cutting element is securely received within the receiving space of the elongate housing;
    a vibrational motor secured within the receiving space of the elongate housing; and
    a power source operatively coupled to the vibrational motor,
    wherein the vibrational motor is operatively coupled to the cutting element within the receiving space of the elongate housing such that, upon activation of the vibrational motor, the cutting portion of the cutting element is configured to vibrate in a single desired plane, and
    wherein the orientation of the vibrational motor within the receiving space of the elongate housing is selectively adjustable to vary the plane in which the cutting portion of the cutting element vibrates.

2. The surgical cutting device of claim 1, further comprising an on-off switch operatively coupled to the vibrational motor, wherein the on-off switch is configured to permit selective activation of the vibrational motor.

3. The surgical cutting device of claim 2, wherein the on-off switch is accessible from outside the receiving space of the elongate housing.

4. The surgical cutting device of claim 3, wherein the on-off switch is selected from the group consisting of a toggle switch, a rotary switch, and a push-button switch.

5. The surgical cutting device of claim 1, wherein the power source is positioned within the receiving space of the elongate housing.

6. The surgical cutting device of claim 5, wherein the power source is a battery.

7. The surgical cutting device of claim 1, wherein the power source is an external power source, and wherein the surgical cutting device further comprises an electrical cable configured to provide operative electrical communication between the vibrational motor and the external power source.

8. The surgical cutting device of claim 1, wherein the vibrational motor operates at a vibrational frequency, and wherein the vibrational frequency is selectively adjustable.

9. The surgical cutting device of claim 1, wherein the receiving space of the elongate housing is configured to receive vibrational motors of varying sizes.

10. The surgical cutting device of claim 1, wherein the receiving space comprises a receptacle that substantially conforms to the shape of the vibrational motor.

11. The surgical cutting device of claim 1, wherein the cutting element is selectively axially moveable relative to the longitudinal axis, thereby permitting adjustment of the axial distance between the cutting portion of the cutting element and the vibrational motor.

12. The surgical cutting device of claim 1, wherein the cutting element is selectively rotatable relative to the longitudinal axis, thereby permitting adjustment of the relative angular orientation between the cutting portion of the cutting element and the vibrational motor.

13. A vibrational assembly for operative coupling to a surgical cutting element, the vibrational assembly having a longitudinal axis and comprising:

an elongate housing having an inner surface and an outer surface, the inner surface of the elongate housing defining a receiving space, the receiving space being configured to securely receive a portion of the surgical cutting element;

a vibrational motor secured within the receiving space of the elongate housing; and a power source operatively coupled to the vibrational motor, wherein the vibrational motor is configured for operative coupling to the cutting element within the receiving space of the elongate housing such that, upon activation of the vibrational motor, the vibrational motor is configured to effect vibration of the cutting element in a single desired plane, and wherein the orientation of the vibrational motor within the receiving space of the elongate housing is selectively adjustable to vary the plane in which the cutting portion of the cutting element vibrates.

14. The vibrational assembly of claim 13, further comprising an on-off switch operatively coupled to the vibrational motor, wherein the on-off switch is configured to permit selective activation of the vibrational motor.

15. The vibrational assembly of claim 14, wherein the on-off switch is accessible from outside the receiving space of the elongate housing.

16. The vibrational assembly of claim 15, wherein the on-off switch is selected from the group consisting of a toggle switch, a rotary switch, and a push-button switch.

17. The vibrational assembly of claim 13, wherein the power source is positioned within the receiving space of the elongate housing.

18. The vibrational assembly of claim 17, wherein the power source is a battery.

19. The vibrational assembly of claim 13, wherein the power source is an external power source, and wherein the vibrational assembly further comprises an electrical cable configured to provide operative electrical communication between the vibrational motor and the external power source.

20. The vibrational assembly of claim 13, wherein the vibrational motor operates at a vibrational frequency, and wherein the vibrational frequency is selectively adjustable.

21. The vibrational assembly of claim 13, wherein the receiving space of the elongate housing is configured to receive vibrational motors of varying sizes.

22. The vibrational assembly of claim 13, wherein the receiving space comprises a receptacle that substantially conforms to the shape of the vibrational motor.

23. The vibrational assembly of claim 13, wherein the elongate housing is configured to permit selective axial movement of the surgical cutting element relative to the longitudinal axis, thereby permitting adjustment of the axial distance between the cutting element and the vibrational motor.

24. The vibrational assembly of claim 13, wherein the elongate housing is configured to permit selective rotation of the surgical cutting element relative to the longitudinal axis, thereby permitting adjustment of the relative angular orientation between the cutting element and the vibrational motor.

* * * * *